United States Patent [19]
Goddard et al.

[11] Patent Number: 4,749,645
[45] Date of Patent: Jun. 7, 1988

[54] HETEROCYCLIC PHOSPHORUS COMPOUND STABILIZERS

[75] Inventors: John D. Goddard; Llewellyn J. Leyshon, both of Harrow, United Kingdom

[73] Assignee: Eastman Kodak Company, Rochester, N.Y.

[21] Appl. No.: 102,697

[22] Filed: Sep. 30, 1987

[30] Foreign Application Priority Data

Oct. 21, 1986 [GB] United Kingdom ............... 8625149

[51] Int. Cl.$^4$ ........................ G03C 7/32; G03C 7/26
[52] U.S. Cl. ................................... 430/551; 430/372; 430/542; 430/546; 430/610
[58] Field of Search ............... 430/546, 551, 372, 931, 430/610, 542

[56] References Cited

U.S. PATENT DOCUMENTS

| | | | |
|---|---|---|---|
| 4,324,856 | 4/1982 | Kawakatsu et al. | 430/610 |
| 4,326,022 | 4/1982 | Ito et al. | 430/546 |
| 4,353,979 | 10/1982 | Terada et al. | 430/372 |
| 4,661,440 | 4/1987 | Tschopp et al. | 430/610 |

FOREIGN PATENT DOCUMENTS 095921 12/1983 European Pat. Off. .

Primary Examiner—Richard L. Schilling
Attorney, Agent, or Firm—Harold E. Cole

[57] ABSTRACT

A photographic element comprising a silver halide emulsion layer having associated therewith a compound having the formula

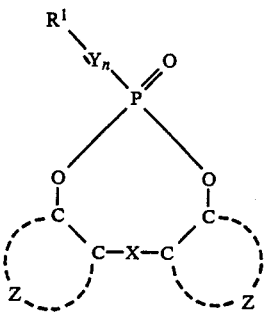

wherein
Y is —O—, —S—, —NH— or —NR$^1$—;
n is 0 or 1;
each R$^1$ independently is the residue of a phosphorus acid;
each Z independently represents the atoms necessary to complete a substituted or unsubstituted benzene ring; and,
X is a single bond or a linking group having a single atom which separates the two benzene rings.

Use of the compound provides increased stability of the dye image obtained during photographic processing.

8 Claims, No Drawings

HETEROCYCLIC PHOSPHORUS COMPOUND STABILIZERS

This invention relates to the stabilization of dye images produced in photographic materials. More particularly, it relates to the use of certain heterocyclic phosphorus compounds as stabilizers for improving the stability of dye images obtained by color developing coupler-incorporated photographic silver halide materials.

A common form of color photographic material comprises red-, green- and blue-sensitive silver halide emulsion layers in or adjacent to which are incorporated cyan-, magenta- and yellow-dye forming couplers, respectively. On development of such a material with a developer containing a p-phenylenediamine color developing agent, the oxidation product produced on reduction of the silver halide by the developing agent reacts with the appropriate coupler to give image dye.

There is a problem with the dye image obtained by color development in that it can deteriorate as a result of the action of light, heat and/or humidity. U.S. Pat. Nos. 4,326,022 and 4,353,979 describe the use of certain high-boiling organophosphorus coupler solvents, and European Patent Application No. 095,921 relates to the use of benzotriazole derivatives and certain high-boiling organophosphorus compounds, which are said to improve the resistance of developed dye images to such deterioration. The heterocyclic phosphorus compounds employed in this invention are structurally different from the organophosphorus coupler solvents employed in the above references and can be employed in photographic elements without putting any restriction on the coupler solvent employed.

According to the invention, heterocyclic phosphorus compounds are employed which can be incorporated in a color photographic material to improve dye stability independently of the coupler solvent used. The compounds confer improved stability on image dyes without causing adverse effects such as fogging, deterioration in color hue and poor dispersion or crystal formation. Further, unlike the high-boiling coupler solvents described in the prior art, the compounds employed in the invention are solids which can be readily obtained in pure form and can be prepared easily at low cost.

In accordance with the invention, a photographic element is provided comprising a support having thereon at least one silver halide emulsion layer having associated therewith a dye stabilizer comprising a compound having the formula

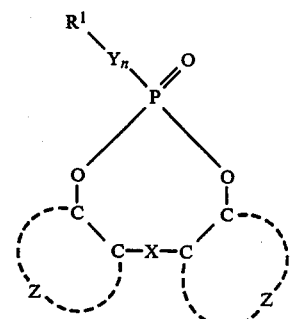

wherein

Y is —O—, —S—, —NH— or —NR¹—;

n is 0 or 1;

each $R^1$ independently is the residue of a phosphorus acid;

each Z independently represents the atoms necessary to complete a substituted or unsubstituted benzene ring; and, X is a single bond or a linking group having a single atom which separates the two benzene rings.

As the residue of a phosphorus acid, $R^1$ may be hydrogen or an aliphatic, aromatic or heterocyclic group. Specific examples of suitable $R^1$ groups include substituted or unsubstituted alkyl, e.g., methyl, ethyl, propyl, butyl or decyl; substituted or unsubstituted cycloalkyl, e.g., cyclohexyl; substituted or unsubstituted alkenyl; and substituted or unsubstituted aryl, e.g., phenyl or naphthyl.

Examples of a linking group for X include substituted or unsubstituted methylene; substituted or unsubstituted alkylidene, e.g., butylidene or 3,5,5,-trimethylhexylidene; a heteroatom, e.g., oxygen or sulphur; and sulfonyl.

In a preferred embodiment of the invention, the stabilizer compounds employed have the formula

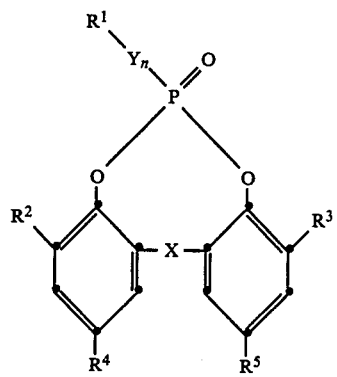

wherein

Y, n, $R^1$ and X are as defined above; and, each of $R^2$, $R^3$, $R^4$ and $R^5$ independently represents hydrogen, a substituted or unsubstituted alkyl group, a substituted or unsubstituted cycloalkyl group, a substituted or unsubstituted alkenyl group, a substituted or unsubstituted aryl group or a heterocyclyl group.

In a preferred embodiment, X is —$CR^6R^7$— in which each of $R^6$ and $R^7$ independently represents hydrogen, a substituted or unsubstituted alkyl group, a substituted or unsubstituted cycloalkyl group, a substituted or unsubstituted alkenyl group, a substituted or unsubstituted aryl group or a heterocyclyl group.

In another preferred embodiment, at least one of $R^6$ and $R^7$ is hydrogen.

In yet another preferred embodiment, $R^2$ and $R^3$ are identical and $R^4$ and $R^5$ are identical.

Specific examples of stabilizers employed in the present invention are as follows:

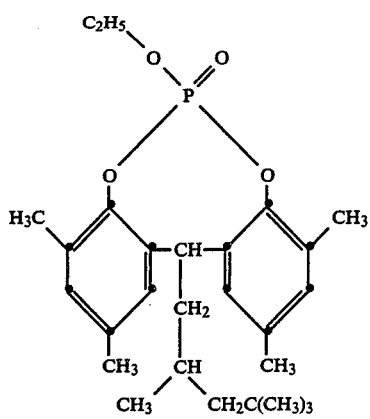
1
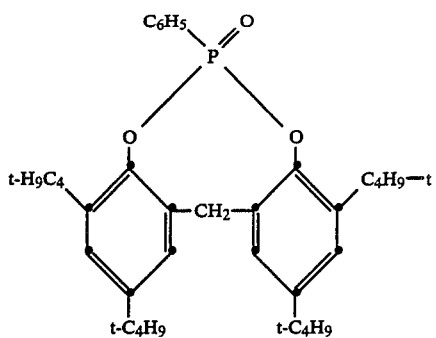
5
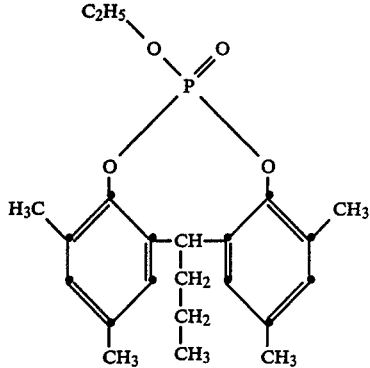
6
2
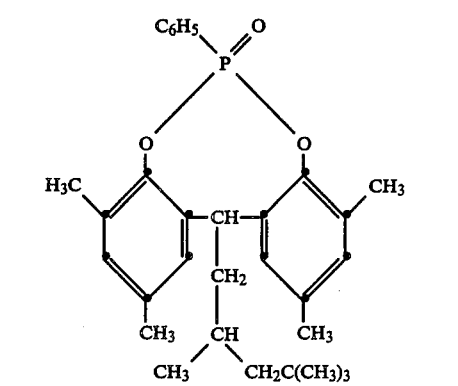
3
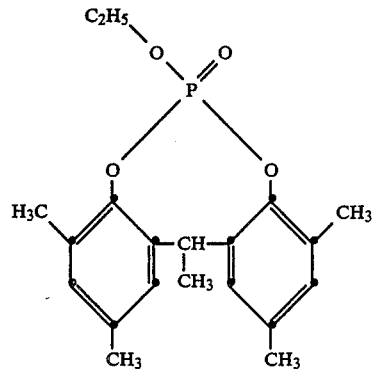
7
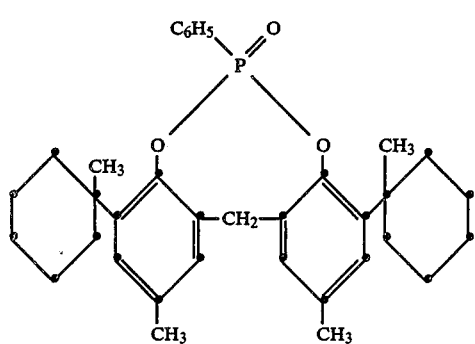
4

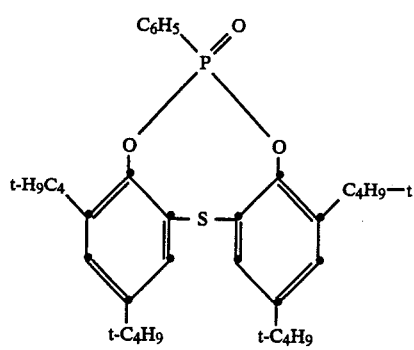
9
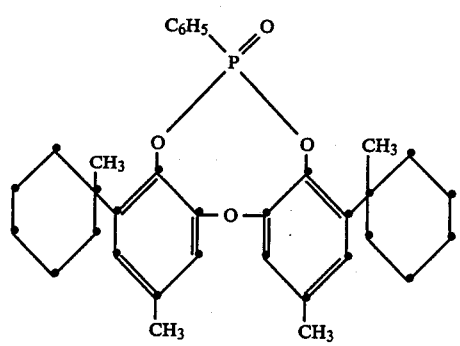
10
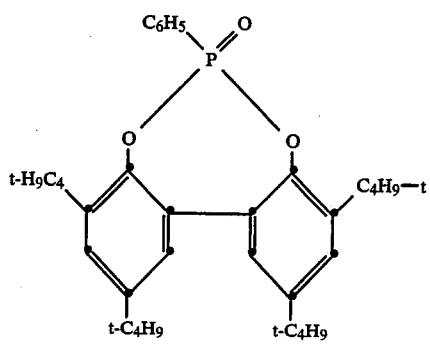
11
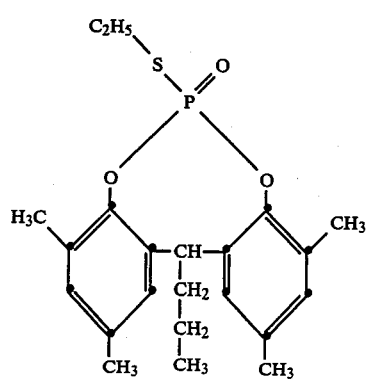
12
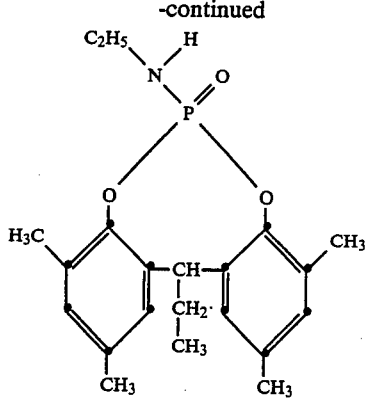
13
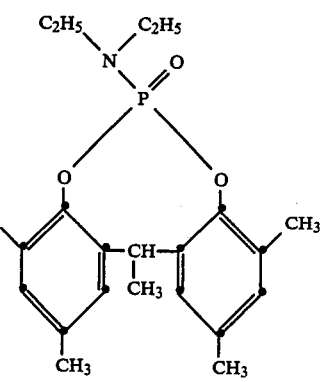
14
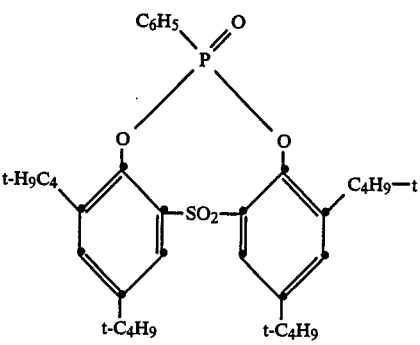
15
The stabilizers employed in the present invention are readily prepared by reacting an appropriate bisphenol compound with an appropriate phosphorus acid dichloride. Many of these starting materials are commercially available. The general reaction may be represented as follows:
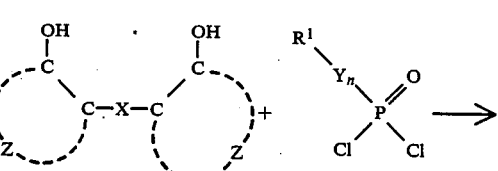

-continued

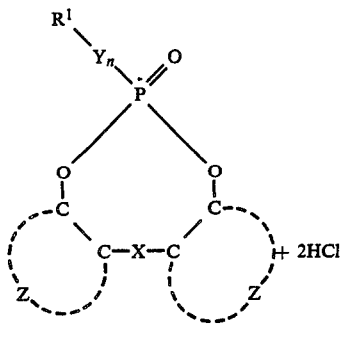

Y, n, R¹, X and Z are as defined above.

Thus, for example, for the preparation of compound 2, the appropriate bisphenol starting material has the formula

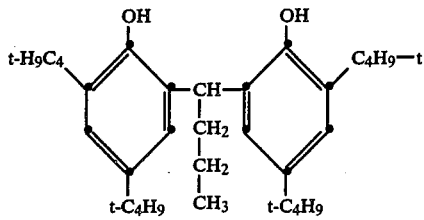

and the appropriate phosphorus acid dichloride is phenylphosphonic dichloride. Reaction of the bisphenol and the acid dichloride may be carried out at room temperature in an inert solvent, e.g., toluene, in the presence of a base, e.g., triethylamine, and a catalyst, e.g., N,N-dimethylaminopyridine.

An alternative synthesis route for preparing compounds employed in the invention may be represented as follows:

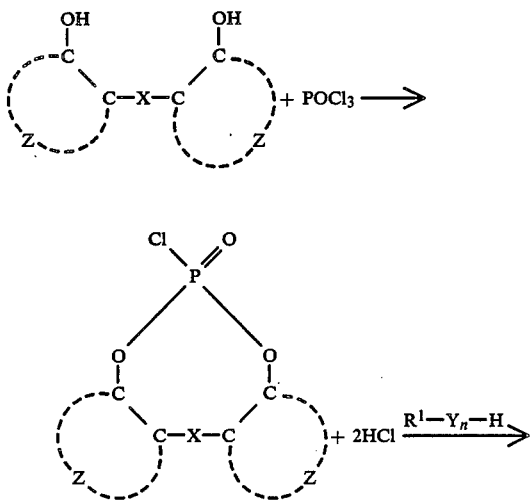

-continued

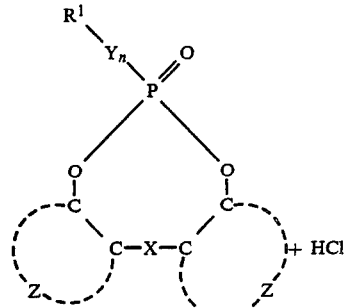

In the above formulae, Y is —O—, —S—, —NH— or —NR¹—, n is 1, and R¹, X and Z are as defined above. Reaction conditions are essentially the same as those suitable for the previous synthesis.

The compounds employed in the invention can be used in any amount sufficient to stabilize the photographic image dyes and their precursors. In general, good results have been obtained using an amount of from about 0.1 to about 2.0 moles per mole coupler, preferably from about 0.5 to about 1.0 mole per mole coupler.

Since the bisphenol derivative is used as a dye stabilizer, it should be incorporated in the silver halide emulsion layer or a layer adjacent thereto. It can be incorporated as a separate dispersion, but is preferably incorporated in admixture with the coupler. Both coupler and stabilizer may be dissolved in a conventional coupler solvent, such as dibutyl phthalate. As in the production of ordinary coupler dispersions, a volatile and/or water-miscible auxiliary solvent, such as ethyl acetate, may be used to aid the dispersion process and then removed by evaporation or by washing the set dispersion. Also, the dispersion process can be assisted by the presence of a surface active compound, as usual in the manufacture of coupler dispersions.

In the following discussion of suitable materials for use in the emulsions and elements of this invention, reference will be made to Research Disclosure, December 1978, Item 17643, published by Industrial Opportunities Ltd., The Old Harbourmaster's, 8 North Street, Emsworth, Hants P010 7DD, U.K., the disclosures of which are incorporated herein by reference. This publication will be identified hereafter as "Research Disclosure". References giving information on couplers and on methods for their dispersions are given in Sections VII and XIV, respectively, of Research Disclosure.

The couplers commonly employed in photographic materials are water-insoluble compounds often containing ballast groups, phenolic (including naphtholic) couplers being used for producing cyan dyes and compounds containing an activated methylene group, including both heterocyclic and open-chain compounds, being used for producing magenta and yellow dyes. Important magenta couplers are pyrazolones and important yellow couplers are benzoylacetanilides. Patents describing couplers include the following U.S. Pat. Nos.:

| Cyan dye-forming | |
|---|---|
| 3,367,531 | 3,034,892 |
| 2,423,730 | 3,311,476 |
| 2,474,293 | 3,419,390 |

| -continued | |
| --- | --- |
| 2,772,826 | 3,458,315 |
| 2,895,826 | 3,476,563 |
| Magenta Dye-forming | |
| 2,343,703 | 3,062,653 |
| 2,369,489 | 3,127,269 |
| 2,600,788 | 3,311,476 |
| 2,908,573 | 3,419,391 |
| 2,933,391 | 3,518,429 |
| Yellow dye-forming | |
| 2,298,443 | 3,277,155 |
| 2,407,210 | 3,408,194 |
| 2,875,057 | 3,415,652 |
| 2,908,573 | 3,447,928 |
| 3,265,506 | 3,933,501 |

An account of dye-forming development is given in "Modern Photographic Processing", Vol. 2, Grant Haist, Wiley, New York, 1978, Chapter 9.

The stabilizers are useful in any coupler-incorporated silver halide photographic materials, including monochrome materials, false-color materials and color transparency, negative and print materials, to stabilize the image dye obtained on development with a solution including a p-phenylene-diamine color developing agent. Such developing agents are described in, for example, Photographic Processing Chemistry, L. F. A. Mason, Focal Press, London, 2nd edition (1975) pp 229-235 and Modern Photographic Processing, Grant Haist, Wiley, New York (1979), Volume 2 pp 463-8.

The silver halide emulsion employed in the elements of this invention can be either negative-working or positive-working. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

The photographic elements of this invention or individual layers thereof, can contain brighteners (see Research Disclosure Section V), antifoggants and stabilizers (see Research Disclosure Section VI), antistain agents and image dye stabilizer (see Research Disclosure Section VII, paragraphs I and J), light absorbing and scattering materials (see Research Disclosure Section VIII), hardeners (see Research Disclosure Section XI), plasticizers and lubricants (see Research Disclosure Section XII), antistatic agents (see Research Disclosure Section XIII), matting agents (see Research Disclosure Section XVI) and development modifiers (see Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

With negative-working silver halide emulsions this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

An example of the preparation of a stabilizer compound used in the present invention is as follows:

Preparation of 2,4,8,10-Tetra-tert-butyl-6-oxo-6-phenyl-12-propyl-12H-dibenzo(d,g)(1,3,2)dioxaphosphocin (Compound 2)

A solution of phenylphosphonic dichloride (10.5 g, 0.054 mole) in dry toluene (30 ml) was added slowly to a solution of 2,2'-butylidenebis(2,4-di-tert-butylphenol) (23.4 g, 0.05 mole) and triethylamine (11.0 g, 0.109 mole) in dry toluene (1 l). After the mixture had stirred for two hours, thin layer chromatography indicated that little or no reaction had occurred. As a result, a catalytic quantity of N,N-dimethylaminopyridine (0.5 g) was added and the mixture stirred overnight. The mixture was filtered and the filtrate washed with dilute hydrochloric acid followed by water. The organic layer was dried using magnesium sulphate and evaporated to dryness under reduced pressure. The light brown residue was slurried in petroleum ether, filtered and then washed with methanol. (Yield=54%, Melting point=232°-34° C.).

Compounds 1 and 3 to 15 may be prepared in an analogous manner.

All the compounds prepared were fully characterized by elemental analysis, nuclear magnetic resonance, thin layer chromatography, high performance liquid chromatography and melting point.

The invention is further illustrated in the following Examples.

EXAMPLE 1

Compound 5, (2,4,8,10-tetra-tert-butyl-6-oxo-6-phenyl-12H-dibenzo[d,g][1,3,2]dioxaphosphocin), (1.27 g, $2.33 \times 10^{-3}$ mole) and the yellow image Coupler I (4.23 g, $4.65 \times 10^{-3}$ mole) were heated with ethyl acetate (3.5 g) and dibutyl phthalate (1.94 g, $6.98 \times 10^{-3}$ mole) were added to the resultant solution.

A 12.5% by weight aqueous gelatin solution containing 0.83% by weight of an alkyl naphthalene sulphonate surfactant ("NEKAL-BX" ® available from BASF) was prepared at 60° C. and mixed with the oil phase solution. The mixture was emulsified with an ultrasonic probe.

Coupler I

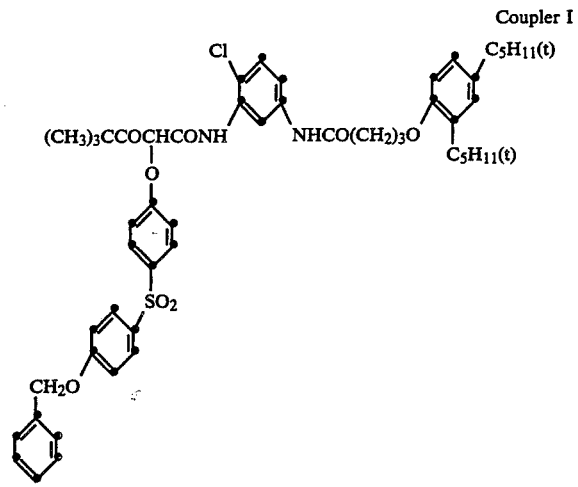

A control dispersion of the Coupler I was prepared in the same way, except that Compound 5 was omitted from the oil phase solution.

The two dispersions were mixed with a silver chlorobromide photographic emulsion and applied to a resin-coated paper support to provide two coatings with the following coverages:

|  | Example 1 | Control |
| --- | --- | --- |
| Ag | 0.398 g/m² | 0.398 g/m² |
| Coupler I | 0.757 g/m² | 0.757 g/m² |
| Compound 5 | 0.228 g/m² | 0 |
| Gelatin | 1.365 g/m² | 1.365 g/m² |

A supercoat containing dioctylhydroquinone (0.054 g/m²) dispersed in gelatin (3.0 g/m²) and containing bisvinylsulphonylmethyl ether (65.4 mg/m²) was applied to protect the photosensitive layers.

Sample strips of the two coatings were exposed through a graduated density test object and developed using a standard Ektaprint-2 process (see British Journal of Photography Annual 1986, pages 37 and 38). Status "A" blue reflection densitometry was used to establish sensitometric curves for the coatings.

The processed strips were exposed to light from a high intensity Xenon source (intensity at the sample plane: 5.4 klux). The samples were protected from UV irradiation by a filter consisting of a coating of Tinuvin 328 ® (Ciba-Geigy) (1.00 g/m²), dispersed in gelatin, on a polyester support. The extent of dye fade for each coating was assessed by comparing sensitometry before and after fading. A convenient representation is afforded by comparison of the density loss from an initial value of 1.7. Table 1 shows the relevant data.

TABLE 1

| Coating | Stabilizer | Fade Time | Density Loss (Di = 1.7) |
| --- | --- | --- | --- |
| Control | None | 6 wk. | −0.35 |
| Example 1 | 5 | 6 wk. | −0.15 |

The results show that Compound 5 improved the stability of the yellow image dye.

EXAMPLE 2

Two coatings were prepared in the same way as described in Example 1 which were identical to the coatings of Example 1 except that Coupler I was replaced with yellow image Coupler II at the same molar level (i.e., weight of Coupler II in the dispersion=2.56 g; coverage=0.459 g/m²).

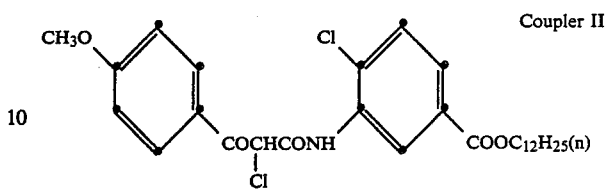

Image dye light stability measurements were made on the coatings using the procedure described in Example 1. Table 2 shows the relevant data.

TABLE 2

| Coating | Stabilizer | Fade Time | Density Loss (Di = 1.7) |
| --- | --- | --- | --- |
| Control | None | 6 wk. | −0.94 |
| Example 2 | 5 | 6 wk. | −0.62 |

The results show that the stability of the image dye was improved by Compound 5.

EXAMPLE 3

Dispersions of yellow image Coupler III with and without Compound 4 (2,10-di(1-methylcyclohexyl)-4,8-dimethyl-6-oxo-6-phenyl-12H-dibenzo[d,g][1,3,2]dioxaphosphocin) were prepared as described in Example 1.

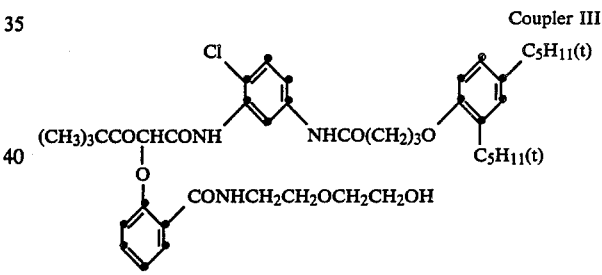

The weights of coupler and stabilizer were adjusted to maintain the molar concentrations specified in Example 1. The dispersions were coated in the same format as described in Example 1, giving a pair of coatings with the following coverages:

|  | Example 3 | Control |
| --- | --- | --- |
| Ag | 0.398 g/m² | 0.398 g/m² |
| Coupler III | 0.661 g/m² | 0.661 g/m² |
| Compound 4 | 0.226 g/m² | 0 |
| Gelatin | 1.365 g/m² | 1.365 g/m² |

Image dye light stability measurements were made on the coatings using the procedure described in Example 1. Table 3 shows the relevant data.

TABLE 3

| Coating | Stabilizer | Fade Time | Density Loss (Di = 1.7) |
| --- | --- | --- | --- |
| Control | None | 8 wk. | −0.22 |
| Example 3 | 4 | 8 wk. | −0.13 |

From the results, it is seen that Compound 4 improved the stability of the image dye.

EXAMPLE 4

Compound 3 (2,4,8,10-tetramethyl-6-oxo-6-phenyl-12H-dibenzo[d,g][1,3,2]dioxaphosphocin) was dispersed with cyan image Coupler IV in an analogous manner to that described in Example 1.

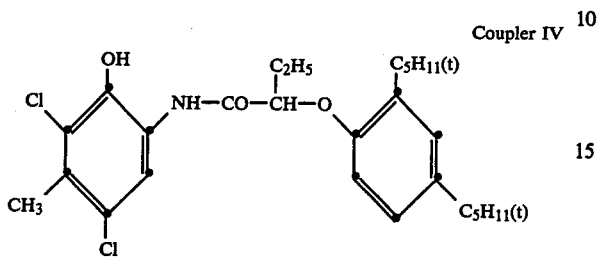

Coupler IV

The quantities of the various components in the oil phase of the dispersion were as follows:

| Coupler IV | 3.70 g (4.75 × 10$^{-3}$ mole) |
|---|---|
| Compound 3 | 3.66 g (4.75 × 10$^{-3}$ mole) |
| dibutyl phthalate | 1.85 g (6.66 × 10$^{-3}$ mole) |
| ethyl acetate | 2.0 g |

A similar control dispersion was prepared omitting Compound 3 from the formulation.

Both dispersions were coated with a photographic emulsion following the procedure set out in Example 1. The coating conditions were adjusted to produce coverages of 663 mg/m$^2$ Coupler IV and 270 mg/m$^2$ Ag.

Sample strips of the coatings were exposed and processed as described in Example 1. Sensitometry was established using red filtration.

The processed strips were incubated in a climatic cabinet controlled at 60° C. and 70% relative humidity (RH) for three weeks. At the end of this time the sensitometric curve was remeasured to monitor the changes in dye density caused by the incubation. In another experiment density changes associated with incubation in an oven controlled at 77° C. were measured in the same way. The density changes measured from an initial value of 1.7 are shown below:

| Stabilizer | Density Loss (Di = 1.7) | |
|---|---|---|
| | 60° C., 70% RH | 77° C. |
| None (Control) | −0.26 | −0.65 |
| Compound 3 | −0.13 | −0.44 |

It is clear that the presence of Compound 3 significantly reduced the loss of dye density under both incubation conditions.

The invention has been described in detail with particular reference to preferred embodiments thereof, but it will be understood that variations and modifications can be effected within the spirit and scope of the invention.

What is claimed is:

1. A photographic element comprising a support having thereon at least one silver halide emulsion layer having associated therewith a dye stabilizer comprising a compound having the formula

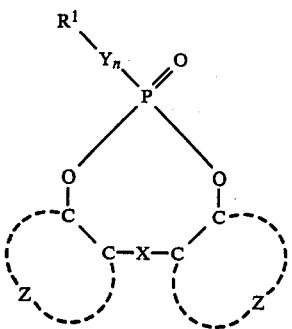

wherein
Y is —O—, —S—, —NH— or —NR$^1$—;
n is 0 or 1;
each R$^1$ independently is the residue of a phosphorus acid;
each Z independently represents the atoms necessary to complete a substituted or unsubstituted benzene ring; and,
X is a single bond or a linking group having a single atom which separates the two benzene rings.

2. The element of claim 1 wherein R$^1$ is a substituted or unsubstituted alkyl group; a substituted or unsubstituted cycloalkyl group; a substituted or unsubstituted alkenyl group; a substituted or unsubstituted aryl group; or a heterocyclyl group.

3. The element of claim 1 wherein X is a substituted or unsubstituted methylene group; a substituted or unsubstituted alkylidene group; a heteroatom; or sulfonyl.

4. The element of claim 1 wherein the compound has the formula

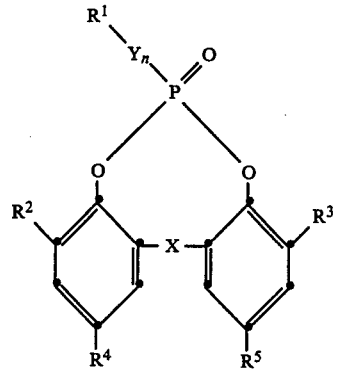

wherein
Y, n, R$^1$ and X are as defined; and,
each of R$^2$, R$^3$, R$^4$ and R$^5$ independently represents hydrogen, a substituted or unsubstituted alkyl group, a substituted or unsubstituted cycloalkyl group, a substituted or unsubstituted alkenyl group, a substituted or unsubstituted aryl group or a heterocyclyl group.

5. The element of claim 4 wherein X is —CR$^6$R$^7$— in which each of R$^6$ and R$^7$ independently represents hydrogen, a substituted or unsubstituted alkyl group, a substituted or unsubstituted cycloalkyl group, a substituted or unsubstituted alkenyl group, a substituted or unsubstituted aryl group or a heterocyclyl group.

6. The element of claim 5 wherein at least one of R$^6$ and R$^7$ is hydrogen.

7. The element of claim 5 wherein R$^2$ and R$^3$ are identical and R$^4$ and R$^5$ are identical.

8. The element of claim 1 wherein said silver halide emulsion layer contains a coupler and said compound is present in an amount of from about 0.1 to about 2.0 moles per mole of said coupler.

* * * * *